United States Patent [19]

Cecco et al.

[11] Patent Number: 4,608,534
[45] Date of Patent: Aug. 26, 1986

[54] EDDY CURRENT PROBE FOR DETECTING LOCALIZED DEFECTS IN CYLINDRICAL COMPONENTS

[75] Inventors: Valentino Cecco; Hugh W. Ghent, both of Deep River, Canada

[73] Assignee: Canadian Patents & Development Limited, Ottawa, Canada

[21] Appl. No.: 504,977

[22] Filed: Jun. 16, 1983

[30] Foreign Application Priority Data

Oct. 22, 1982 [CA] Canada .................................. 414020

[51] Int. Cl.[4] ...................... G01N 27/90; G01R 33/12
[52] U.S. Cl. .................... 324/238; 324/220; 324/262; 324/DIG. 1; 336/84 C
[58] Field of Search ............................... 324/219-221, 324/224, 225, 228-231, 233-243, DIG. 1, 262; 174/35 CE; 336/84 C, 73; 335/214, 301

[56] References Cited

U.S. PATENT DOCUMENTS

| | | | |
|---|---|---|---|
| 1,370,731 | 3/1921 | Chase | 174/35 CE |
| 2,104,646 | 1/1938 | Greenslade | 324/219 |
| 2,162,710 | 6/1939 | Gunn | 324/233 |
| 2,463,778 | 3/1949 | Kellogg | 174/35 CE |
| 2,565,191 | 8/1951 | Zenner | 174/35 CE |
| 2,855,564 | 10/1958 | Irvin et al. | 324/242 |
| 3,075,144 | 1/1963 | Cooper | 324/219 |
| 3,094,658 | 6/1963 | Bravenec et al. | 324/233 X |
| 3,197,693 | 7/1965 | Libby | 324/225 |
| 3,521,158 | 7/1970 | Morrow et al. | 324/236 |
| 3,611,120 | 10/1971 | Förster | 324/225 |
| 3,707,671 | 12/1972 | Morrow et al. | 324/236 X |
| 3,737,764 | 6/1973 | Dufayet | 324/237 |
| 3,753,096 | 8/1973 | Wiers | 324/233 |
| 3,840,802 | 10/1974 | Anthony | 324/219 |
| 3,952,315 | 4/1976 | Cecco | 324/220 |
| 3,996,510 | 12/1976 | Guichard | 324/236 X |
| 4,079,312 | 3/1978 | Osborn et al. | 324/226 |
| 4,083,602 | 4/1978 | Allport | 324/227 |
| 4,087,774 | 5/1978 | Beuchat | 336/73 |
| 4,176,334 | 11/1979 | Buritz et al. | 336/84 C |
| 4,204,159 | 5/1980 | Sarian et al. | 324/232 |
| 4,233,583 | 11/1980 | Novacek | 335/301 X |

FOREIGN PATENT DOCUMENTS

| | | |
|---|---|---|
| 924383 | 4/1973 | Canada . |
| 520328 | 4/1940 | United Kingdom . |
| 668177 | 3/1952 | United Kingdom . |
| 886760 | 1/1962 | United Kingdom . |
| 1079913 | 8/1967 | United Kingdom . |
| 1378711 | 12/1974 | United Kingdom . |
| 1601977 | 11/1981 | United Kingdom . |

Primary Examiner—Gerard R. Strecker
Assistant Examiner—Warren S. Edmonds
Attorney, Agent, or Firm—Edward Rymek

[57] ABSTRACT

Eddy current probes which are used to internally or externally inspect cylindrical components for localized defects have a main coil arrangement that induces and senses eddy current in the components. In accordance with the present invention, the probe further includes an element associated with the main coil arrangement to generate a detected defect signal distinct from a detected noise signal. The element can include one or more further coils mounted coaxially with the main coil arrangement so as to be between the main coil arrangement and the component to be inspected. The element may alternately be a cylindrical conductive sleeve mounted coaxially with the main coil arrangement so as to partially shield the coil arrangement from the component to be inspected. An electrical phase shifting network may be connected to the one or more further coils to enhance the distinction between the signals.

6 Claims, 14 Drawing Figures

EDDY CURRENT PROBE FOR DETECTING LOCALIZED DEFECTS IN CYLINDRICAL COMPONENTS

BACKGROUND OF THE INVENTION

This invention is directed to eddy current probes for internal or external inspection of tubes or other cylindrical components, and in particular, to probes for providing defect signals which may be distinguished from noise signals.

Conventional bobbins or encircling probes are normally effective in inspecting cylindrical or tubular components. Examples of these are U.S. Pat. No. 2,855,564, which issued on Oct. 7, 1958, to E. M. Irvin et al; U.S. Pat. No. 3,952,315, which issued on Apr. 20, 1976, to V. S. Cecco; U.S. Pat. No. 4,079,312, which issued on Mar. 14, 1978, to M. L. Osborn et al; U.S. Pat. No. 4,083,002, which issued on Apr. 4, 1978, to J. J. Allport.

In order to be able to internally inspect components, such as heat exchanger tubes, for internal defects in the presence of probe wobble or internal tube variation, such as tube distortion created by the 'pilger' tube reduction process, a probe which will produce a defect signal that is different than a noise signal, is needed. U.S. Pat. No. 3,197,693, which issued on July 27, 1965, to H. L. Libby, and U.S. Pat. No. 3,753,096, which issued on Aug. 14, 1973, to W. C. Wiers, are examples of probes in which attempts are made to compensate for the noise problem caused by lift-off. U.S. patent application Ser. No. 283,092, filed by H. W. Ghent et al on July 13, 1981, which corresponds to Canadian patent application No. 359,392, filed on Aug. 18, 1980, describes an eddy current surface probe which provides different defect and noise signals when the probe is used to test surfaces. These probes cannot be readily applied to the internal or external inspection of tubes or cylindrical components.

SUMMARY OF THE INVENTION

It is therefore an object of this invention to provide eddy current probes for the inspection of tubes or other cylindrical components, which will provide defect and noise signals that are distinct from one another.

This and other objects are achieved in eddy current probes which are used to internally or externally inspect cylindrical components for localized defects. These probes have coil arrangements which induce and sense eddy currents in the components to be inspected. The probe, in accordance with the present invention, includes an element associated with the coil arrangement in order to generate a detected defect signal distinct from a detected noise signal.

In accordance with one aspect of this invention, the element includes one or more further coils mounted sequentially along a common axis and coaxially with the coil(s) in the main coil arrangement so as to be located between the main coil arrangement and the component to be inspected. The further coil(s) may be shorter than the coil(s) in the main coil arrangement.

In accordance with a further aspect of the present invention, the element may further include an electrical phase shifting network connected to at least one of the further coils to enhance the signal distinction.

In accordance with another aspect of this invention, the element may alternately be a cylindrical electrically conductive sleeve mounted coaxially with the main coil arrangement so as to partially shield the main coil arrangement from the component to be inspected. This element may also include one or more further coaxial coils with or without the electrical phase shifting network to the further coils.

Many other objects and aspects of the invention will be clear from the detailed description of the drawings.

DETAILED DESCRIPTION

Two basic circuits are used in the eddy current testing or conductive components. The first, illustrated in FIG. 1, consists of an AC bridge 11 in which at least one arm 12, 13, 14 or 15, and normally two arms, includes coils which are located in the eddy current probe. The other arms having adjustable impedances. An AC source 16, which normally would be adjustable in frequency, is connected across the bridge 11 to energize the bridge 11 which is balanced by adjusting the impedances. A detector 17 is connected across the bridge 11 and is used to detect the null point when balancing the bridge 11 and to detect any unbalance caused by noise or defects.

Figure 2:
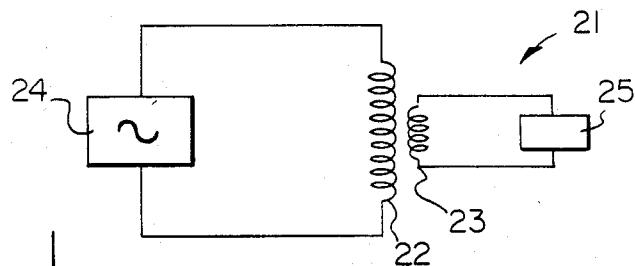

The second eddy current testing circuit which is shown in FIG. 2, is commonly known as a send-receive instrument 21. It includes excitation coils 22 which are coupled through the work piece to receive coils 23. All of these coils 22 and 23 are located in the eddy current probe. The excitation coils 22 are connected to an adjustable AC source 24, while the receive coils are connected to a detector 25.

Figure 3:
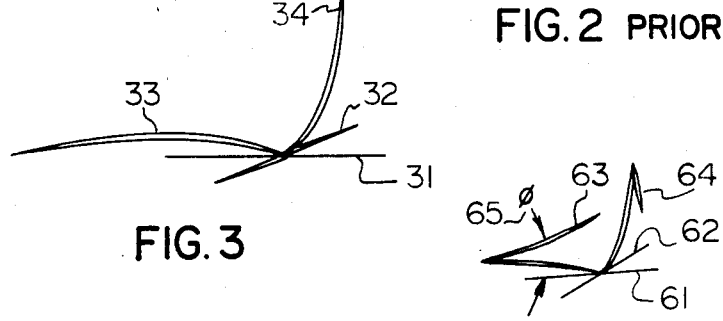
FIG. 3 illustrates a plot of the signal produced by absolute type conventional probes.

This type of apparatus, using conventional probes, produces signals which may be confusing. Examples of x-y plotted signals for an internally inspected tube, using an absolute probe, are illustrated in FIG. 3. Signal 31 represents tube deformation or Pilger noise, signal 32 represents probe wobble noise, signal 33 represents an internal defect and signal 34 represents an external defect. There is very little phase separation between signals from internal defects 33 and internal tube noise 31 or 32. These would be very difficult to distinguish, particularly if they occurred simultaneously. It is noted, however, that there is excellent phase separation between signals from external defects 34 and internal tube noise 31 or 32.

The probes, in accordance with the present invention, can use the same probe casing structures as conventional probes and can be utilized with conventional eddy current circuits. During inspections, they produce signals in which the defect signals appear rotated in phase relative to the noise signals. The present probe coil arrangements are constructed by one or more of the following novel techniques: by adding one or more further coils to the coil arrangement such that one coil is more sensitive to defects than another coil, this technique may be enhanced by connecting an electrical phase shifting circuit to at least one of the further coils; or, by adding a conductive sleeve to partially shield one or more coils.

Figure 4:
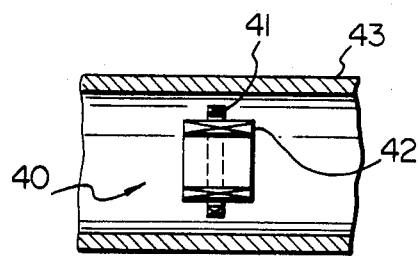
FIGS. 4, 5, 7 and 8, illustrate coil arrangements with additional coils.
Figure 5:
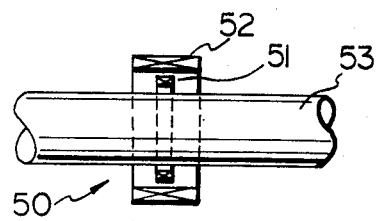

Coil arrangements 40 and 50 for inner and outer inspection absolute probes are illustrated in FIGS. 4 and 5, respectively. Arrangement 40 consists of a pair of co-axial coils 41 and 42, both sensing the test material wherein the coil 41, which is nearest the cylindrical component 43, is shorter than the remote coil 42. Coil arrangement 50 also includes a pair of co-axial coils 51 and 52, with the shorter coil 51 nearest the cylindrical component 53, and the longest coil 52 remote from it. For some applications, it might prove advantageous to have the longest coil nearest the cylindrical component.

Figure 1:
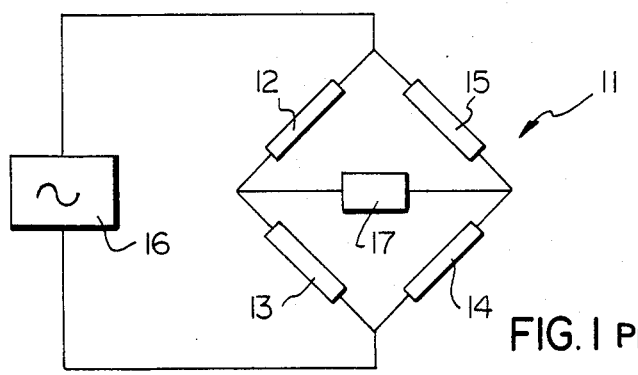
FIGS. 1 and 2 illustrate conventional eddy current instruments.

The coils are connected on adjacent arms of an AC bridge, such as arms 14 and 15 in FIG. 1. Since the coils have significantly different lengths but similar diameters, the defect or noise signal from one coil will be rotated only slightly relative to the signal from the other coil. However, the sensitivity to short defects is greater for the short coil nearest the test component, resulting in a large residual signal when the probe traverses a defect. By appropriate choice of coil parameters, the sensitivity to the tube variation or noise can be made approximately equal, resulting in a small residual signal. The ratio of a defect signal to noise signal is significantly increased. This coil arrangement works best for localized defects where the defect length is comparable to or shorter than the length of the short coil and the tube deformation is longer than the short coil.

Figure 6:
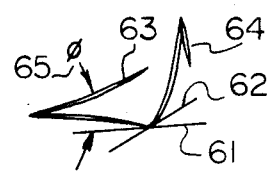
FIG. 6 is a plot of the signals produced by a probe having the coil arrangement shown in FIG. 4.

FIG. 6 illustrates typical x-y signals obtained from an internal inspection probe having a coil arrangement 40 shown in FIG. 4, wherein 61 is the deformation noise signal, 62 is the wobble noise signal, 63 is an internal defect signal, and, 64 is an external defect signal. For this coil arrangement, the maximum practical phase ($\phi$) separation 65 is approximately 30°.

Figure 7:
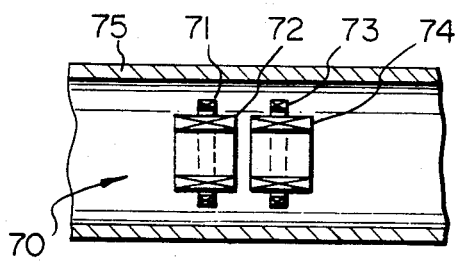

A similar differential type inspection coil arrangement 70 is shown in FIG. 7, which is used for internally inspecting a component 75. Coil arrangement 70 includes a pair of identical near coils 71, 73, and a pair of identical remote coils 72, 74, whch are located co-axially within coils 71, 73. When used as a bridge instrument, coils 71 and 72 would be connected in series in one arm of the bridge, and coils 73 and 74 would be connected in series in an adjacent arm of the bridge.

Figure 8:
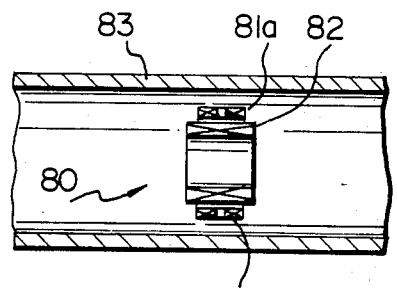

A further embodiment of an external inspection absolute coil arrangement is shown in FIG. 8, in which the coil arrangement 80 includes a single inner coil 82 and a number of surface coils 81a, 81b, 81c, . . . positioned about the outside of near coil 82. In FIG. 8, two surface coils 81a and 81c are shown for a four surface coil system. The outer surface coils are all connected in series.

Surface coils 81a, 81b, 81c, . . . have drastically different diameters than inner coil 82. This would result in a defect signal significantly rotated from that of the inner coil. The signal noise phase separation, 65 (FIG. 4), could be as large as 45°-60°. For such a large phase separation, the noise signal decreases only slightly in amplitude. This coil arrangement has another important advantage over arrangement 40 in its ability to detect circumferential cracks.

Figure 9:
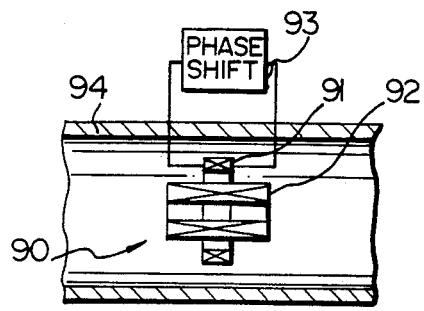
FIG. 9 illustrates a coil arrangement with phase shifting circuits.

In the above probes, where further coils have been added to the coil arrangements, the distinction between noise and defect signals may be enhanced by connecting a phase shifting network to the coil or coils. An example of such a coil arrangement for an absolute external inspection probe is illustrated in FIG. 9. The coil arrangement 90 consists of a pair of coaxial coils 91, 92, both sensing the test material, with a phase shifting network 93 to the outer coil 91. The variable passive electrical components in the phase shifting network 93 can be sent such that the bridge remains balanced, and the current passing through coil 91 is phase shifted relative to the current passing through coil 92. By this means, all signals detected by the coil with the phase shifted current will be rotated by an amount equal to the phase shift, relative to those signals detected by the coil without phase shifted currents. Such a phase shifting network 93, could be added to the test coil of any of the coil arrangement where further coils are added, such as the coil arrangements 40, 50, 70, and 80.

Figure 10:
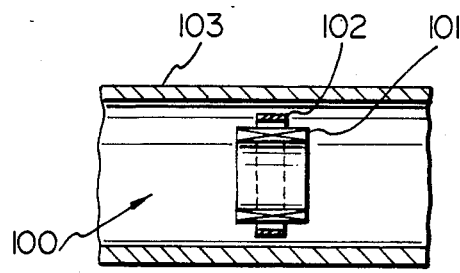
FIGS. 10, 12 and 13 illustrate coil arrangements with a partially shielding sleeve.

The second technique creating the distinct defect and noise signals is illlustrated by the coil arrangement 100 in FIG. 10, for internally inspecting a cylindrical component 103. Arrangement 100 includes a test coil (reference coil is not included in FIG. 10) with an electrically conductive sleeve placed over a portion of it. This coil arrangement works best for localized defects where the defect length is comparable to or shorter than the length of the conducting sleeve and the tube deformation is longer than the conducting sleeve.

The conducting sleeve 102, made of copper or other electrically conducting material, covers ⅛ to ½ of the test coil 101. The sleeve thickness is approximately equal to or less than one skin depth, where one skin depth, $\delta$, is given by:

$$\delta = 50 \, (\rho/f)^{\frac{1}{2}}, \text{ mm}$$

where $\rho$ is electrical resistivity, $\mu\Omega$cm
and, f is test frequency, hertz.

The defect signal from the partially shielded section of the coil rotates clockwise relative to the unshielded part of the coil. This is due to the magnetic flux (and eddy currents) phase lag and attenuation across the conducting sleeve. The phase lag ($\beta$) is given by:

$$\beta = t/\delta, \text{ radians}$$

where t is sleeve thickness, mm.

Figure 11:
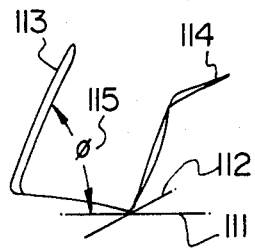
FIG. 11 illustrates signals produced by a probe having the coil arrangement shown in FIG. 10.

FIG. 11 illustrates typical X-Y signals obtained from an internal inspection probe having coil arrangement 100 shown in FIG. 10, wherein 111 is deformation noise signal, 112 is the wobble signal, 113 is an internal defect signal, and 114 is an external defect signal. For this coil arrangement, the optimum phase separation, 115, of 90° between defect and noise signal can be readily achieved. As expected, the noise signal 111 also rotates some as the defect signal rotates.

Figure 12:
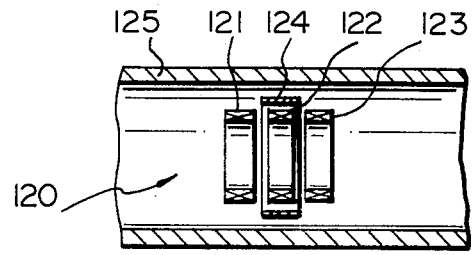

A further embodiment of a coil arrangement 120 for an absolute probe is illustrated in FIG. 12. It consists of three side-by-side coils 121, 122, 123, with a sleeve 124 partially shielding the center coil 122. For an internal inspection probe, the sleeve 124 is placed adjacent the outside surface of coil 122, as shown, while for an external inspection probe, the sleeve 124 is placed adjacent the inside surface of the coil 122. Coils 121 and 123 would be connected in series in one arm of an AC bridge instrument, while coil 122 would be connected in an adjacent arm of the bridge.

Figure 13:
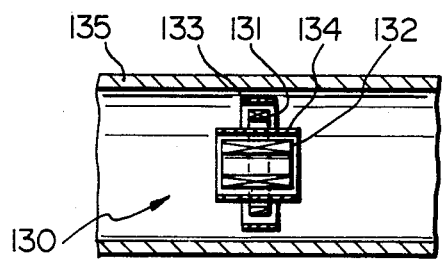

An embodiment of a coil arrangement combining the first and second method of rotating a defect related signal is illustrated by the coil arrangement 130 in FIG. 13. The coil arrangement 130 is similar to coil arrangement 40 except for the conducting sleeves 133 and 134. Conducting sleeve 133 is used to rotate cw defect signal from coil 131 and conducting sleeve 134 is used to rotate cw defect signal from coil 132. By appropriate choice of one or both conducting sleeves, a defect signal, such as 63 in FIG. 6, can be rotated to achieve the desired phase ($\phi$) separation 65 of approximately 90°. In addition to achieving the desired phase separation, the 'noise' signal can be significantly decreased.

Figure 14:
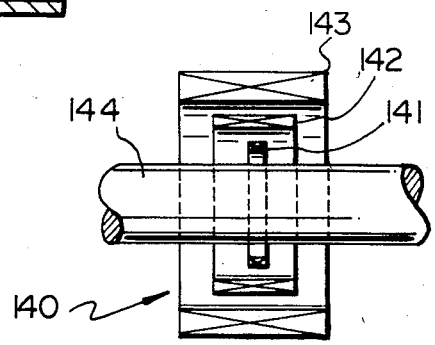
FIG. 14 illustrates a coil arrangement for a send-receive probe.

A further coil arrangement 140 for an external inspection absolute send-receive probe is illustrated in FIG. 14. The excitation coil 143 is the outer coil and the two receive coils 141 and 142 are the inner coils. Coils 141 and 142 would be wound in opposition resulting in eddy current defect signals similar to coils connected on adjacent arms of an AC bridge in an impedance type system. All of the coil arrangements 40, 50, 70, 80, 90, 120 and 130 would work in a send-receive system, with the addition of an excitation coil.

Many modifications in the above described embodiments of the invention can be carried out without departing from the scope thereof and, therefore, the scope of the present invention is intended to be limited only by the appended claims.

We claim:

1. In an eddy current probe for internally or externally inspecting cylindrical components to detect a localized defect, a coil arrangement having two or more coils each having a predetermined axial length, connected in two arms of a four arm AC bridge detector circuit such that a least a first of the coils induces and senses eddy currents in a cylindrical component to be inspected, wherein the probe further includes a first thin cylindrical electrically conductive sleeve positioned coaxially with the first coil, so as to be located between the first coil and the cylindrical component, the sleeve being narrower than the axial length of the first coil and positioned symmetrically with respect to the axial length of the first coil to distort the induced eddy currents in phase and amplitude thereby generating a detected signal due to the localized defect in the cylindrical component that is distinct from detected noise signals.

2. In an eddy current probe as claimed in claim 1 in which a second coil substantially identical to and mounted coaxially and adjacent to the first coil, is electrically differentially connected to the first coil, and a second thin cylindrical electrically conductive sleeve, substantially identical to the first conductive sleeve, positioned coaxially with the second coil so as to be located between the second coil and the cylindrical component and positioned symmetrically with respect to the axial length of the second coil.

3. An eddy current probe as claimed in claim 1 in which the sleeve thickness $t \leq 50 \, (\rho/f)^{\frac{1}{2}}$ where
$\rho$ = electrical resistivity of the sleeve, and
$f$ = frequency of the AC detector.

4. An eddy current probe as claimed in claim 1 in which the sleeve width is approximately $\frac{1}{2}$ to $\frac{1}{3}$ the length of the associated coil.

5. An eddy current probe as claimed in claim 2 in which the thickness t of each sleeve $\leq 50 \, (\rho/f)^{\frac{1}{2}}$ where
$\rho$ = electrical resistivity of the sleeve, and
$f$ = frequency of the AC detector.

6. An eddy current probe as claimed in claim 2 in which the width of each sleeve is approximately $\frac{1}{2}$ to $\frac{1}{3}$ the length of the associated coil.

* * * * *